US011253293B2

(12) United States Patent
Al-Habaibeh et al.

(10) Patent No.: US 11,253,293 B2
(45) Date of Patent: Feb. 22, 2022

(54) FLUID VESSEL COMMUNICATION DEVICE

(71) Applicants: Olberon Limited, Nottinghamshire (GB); Nottingham Trent University, Nottingham (GB)

(72) Inventors: Amin H. A. Al-Habaibeh, Nottingham (GB); Arash Bakhtyari-Nejad-Esfahani, Nottingham (GB); Thomas David Stead, Nottingham (GB)

(73) Assignee: OLBERON LIMITED, Nottinghamshire (GB)

( * ) Notice: Subject to any disclaimer, the term of this patent is extended or adjusted under 35 U.S.C. 154(b) by 0 days.

(21) Appl. No.: 15/802,114

(22) Filed: Nov. 2, 2017

(65) Prior Publication Data

US 2018/0064465 A1 Mar. 8, 2018

Related U.S. Application Data

(63) Continuation of application No. 14/003,745, filed as application No. PCT/GB2012/050530 on Mar. 9, 2012, now abandoned.

(30) Foreign Application Priority Data

Mar. 9, 2011 (GB) .................................... 1104016

(51) Int. Cl.
*A61B 17/34* (2006.01)
*A61M 25/06* (2006.01)
*A61M 5/158* (2006.01)

(52) U.S. Cl.
CPC ...... *A61B 17/3415* (2013.01); *A61B 17/3496* (2013.01); *A61M 5/158* (2013.01); *A61M 25/0612* (2013.01); *A61M 25/0693* (2013.01)

(58) Field of Classification Search
CPC .. A61M 5/322; A61M 5/3221; A61M 5/3232; A61M 5/3234; A61M 2005/3235;
(Continued)

(56) References Cited

U.S. PATENT DOCUMENTS 2,198,666 A 4/1940 Gruskin
2,457,464 A 12/1948 Grose
(Continued)

FOREIGN PATENT DOCUMENTS

CN 201179084 1/2009
GB 2487899 8/2012
(Continued)

OTHER PUBLICATIONS

International Search Report issued in PCT Application No. PCT/GB2012/050530, dated May 31, 2012, in 4 pages.
(Continued)

*Primary Examiner* — William R Carpenter
(74) *Attorney, Agent, or Firm* — Moser Taboada

(57) ABSTRACT

A fluid vessel insertion device (10), typically for medical use, comprises a puncture member (18) arranged for locaton within a sleeve (20), and a retraction mechanism (44, 48, 60) for retracting the puncture member relative to the sleeve. The puncture member (18) is retractable in use between a first condition in which an end (18A) of the puncture member protrudes beyond an end (24) of the sleeve and a second condition in which the end of the puncture member is within the sleeve (20). The retraction mechanism (44, 48, 60) actuates the puncture member between the first and second conditions in response to fluid pressure at the end (18A) of the puncture member. The device may be used during positioning of the sleeve in a desired fluid vessel, such as, for example, during intravenous cannulation.

19 Claims, 7 Drawing Sheets

(58) Field of Classification Search
CPC .. A61M 2005/3236; A61M 2005/3238; A61M 2005/3239; A61M 25/0606; A61M 25/0612; A61M 25/0618; A61M 25/0631
See application file for complete search history.

(56) References Cited

U.S. PATENT DOCUMENTS

| | | | |
|---|---|---|---|
| 5,129,884 A | 7/1992 | Dysarz | |
| 5,158,552 A | 10/1992 | Borgia et al. | |
| 5,207,647 A * | 5/1993 | Phelps | A61B 17/3401 604/158 |
| 5,312,361 A * | 5/1994 | Zadini | A61M 5/158 604/165.02 |
| 5,454,791 A | 10/1995 | Tovey et al. | |
| 5,514,096 A * | 5/1996 | Hiejima | A61M 5/152 604/132 |
| 5,527,290 A | 6/1996 | Zadini et al. | |
| 5,573,510 A | 12/1996 | Isaacson | |
| 5,733,265 A | 3/1998 | Bachman et al. | |
| 5,902,273 A | 5/1999 | Yang et al. | |
| 6,221,048 B1 | 4/2001 | Phelps | |
| 6,514,177 B1 * | 2/2003 | Brugger | F04B 43/0054 482/13 |
| 6,626,868 B1 * | 9/2003 | Prestidge | A61M 25/0631 604/158 |
| 7,175,608 B2 | 2/2007 | Hasan et al. | |
| 7,867,173 B2 | 1/2011 | Hibner et al. | |
| 9,347,533 B2 | 5/2016 | Eller | |
| 2003/0073952 A1* | 4/2003 | Flaherty | A61M 5/14248 604/151 |
| 2003/0181861 A1 | 9/2003 | Wilkinson | |
| 2004/0106903 A1 | 6/2004 | Shue et al. | |
| 2006/0173480 A1 | 8/2006 | Zhang | |
| 2007/0021724 A1 | 1/2007 | Bressler et al. | |
| 2007/0032741 A1 | 2/2007 | Hibner et al. | |
| 2009/0209912 A1 | 8/2009 | Keyser et al. | |
| 2009/0259143 A1 | 10/2009 | Bakhtyari-Nejad-Esfahani | |
| 2013/0338577 A1 | 12/2013 | Al-Habaibeh et al. | |
| 2014/0183670 A1* | 7/2014 | Millett | G01L 19/147 257/415 |

FOREIGN PATENT DOCUMENTS

| | | |
|---|---|---|
| JP | 10-151206 | 6/1998 |
| WO | WO 93/05832 | 4/1993 |
| WO | WO 2003/003908 | 1/2003 |
| WO | WO 2009/021170 | 2/2009 |

OTHER PUBLICATIONS

Search Report issued in GB Application No. 1104016.9, dated Sep. 9, 2011, in 2 pages.

* cited by examiner

FLUID VESSEL COMMUNICATION DEVICE

The present invention relates to a fluid vessel communication device and more particularly to a device for insertion into a vessel so as to allow fluid communication with the interior of the vessel. Such devices may be used in medical applications although they are not limited thereto.

In order to communicate with an existing fluid vessel it is often required to puncture a vessel wall so as to provide a port therein. In the event that ongoing fluid communication is required with the vessel, it may be required to establish a vessel junction such that the puncturing member has to be removed and replaced with a more suitable fluid conduit, which, for example, carries a reduced risk of causing further unwanted damage to the vessel.

Within the medical field, there are a number of scenarios in which it is necessary to puncture fluid vessels in the manner described above for delivery of fluid to, or removal of fluid from, a fluid vessel in the body.

Intravenous cannulation is a common example of such a medical procedure. It is estimated that there are at least 25 million cannulations a year in the UK alone. Intravenous cannulation is expected routinely to fail in 20-30% of initial attempts and can prove to be problematic for certain patient groups or inexperienced operators.

The inventors have determined that at least a portion of failed cannulation attempts can be attributed to the fact that the walls of fluid vessels in the body, such as blood vessels, often do not offer a significant increase in resistance to the travel of a needle compared to the surrounding tissue. Also the depth of the vessel to be punctured may be relatively small such that the operator has little scope for error when attempting to position the needle end with in the vessel. The combination of a small target zone and low tactile feedback mean that operators frequently do not realise when a needle is correctly located in a vein and may insert a needle through the vein and thereby fail in the correct positioning of both the needle and cannula.

Even if an operator does correctly interpret the point at which the vessel is punctured, there remains the possibility that any unintentional movement of the operator or a patient thereafter could cause further puncturing of the vessel, for example through the opposing vessel wall, resulting in a failed cannulation attempt.

Effort has been expended in the past to provide devices which present additional feedback to an operator to aid in determining the location of a needle within the body. U.S. Pat. No. 7,175,608 provides an example of such a device, which is specific to the detection of the negative pressure within the epidural space, and which aims to provide a visual indication of correct needle positioning to an operator.

However the provision of a visual indication of correct needle positioning to an operator in order to supplement the relatively low level of tactile feedback only provides a partial solution to the problems discussed above. Furthermore a visual indication can draw an operator's focus away from the precise point of insertion and the advancement of the needle therein.

It is an aim of the present invention to provide a fluid vessel insertion device which allows for improved accuracy and/or reliability of insertion.

According to the present invention there is provided a fluid vessel insertion device comprising a puncture member arranged for location within a sleeve, and a retraction mechanism for retracting the puncture member relative to the sleeve in use between a first condition in which an end of the puncture member protrudes beyond an end of the sleeve and a second condition in which the end of the puncture member is within the sleeve, wherein the retraction mechanism actuates the puncture member between the first and second conditions in response to fluid pressure at the end of the puncture member.

Fluid pressure may be considered to comprise any or any combination of static or dynamic fluid pressure and may be separate from the contact or friction force experienced by the puncture member due to passage through a vessel wall or surrounding material.

The determination of fluid pressure as the trigger for retraction of the puncture member is advantageous since it allows accurate assessment of the point of entry of the puncture member into a vessel of generally known or predictable internal fluid pressure. The determination may be made based on a deviation of fluid pressure form an ambient fluid pressure level. The determination is advantageously not reliant on feedback pertaining to the resistance of the vessel wall to puncturing.

Furthermore the retraction of the puncture member relative to the sleeve requires minimal movement and/or retraction force. Thus the sleeve can reliably remain in the desired position within a vessel with minimal disturbance.

The retraction mechanism may be actuated in response to a positive fluid pressure at the end of the puncture member, for example due to a fluid pressure at the end which is greater than atmospheric pressure and/or greater than a fluid pressure level within the device, or a part thereof, such as an internal chamber, which may be within the device.

The sleeve may be mounted in a fixed position/orientation with respect to any, or any combination, of the device, the retraction mechanism, the chamber and/or the device housing. The sleeve may be mounted to a support formation, which is in turn removably attachable to the device to provide the desired orientation in use but which is detachable there-from once the puncture member has been retracted.

The puncture member may be shaped to allow fluid communication with the retraction mechanism. Typically the puncture member is hollow and allows for the passage of fluid therein. The puncture member may be elongate and/or tubular in form. The puncture member may be tapered towards a sharp end and may comprise a needle or trocar.

A hollow puncture member allows fluid pressure at the end of the puncture member to be determined at a spaced location. The retraction mechanism may comprise a chamber in communication with the interior of the puncture member. Accordingly the fluid pressure at the end of the puncture member may be experienced by the chamber.

The chamber may be located within a body or housing of the device. The chamber may be maintained at a first, typically atmospheric, pressure in an at-rest condition, which may correspond to the first condition of the retraction mechanism. The chamber may have an actuated condition, which may correspond to the second condition of the retraction mechanism. The change from the first to the second condition of the chamber and/or retraction mechanism may be caused by the elevation of the pressure within the chamber to above the first condition. This may correspond to a positive pressure gradient or differential existing between the interior of the chamber and the fluid pressure at the end of the puncture member.

The chamber may comprise one or more deformable walls or formations, which may be actuable in response to the pressure within the chamber. The chamber may comprise a diaphragm. Movement of the diaphragm may trigger the retraction mechanism. A diaphragm has been found to provide a particularly sensitive and responsive trigger/actuator in response to typical vascular fluid pressures. The volume of the chamber and size of the diaphragm, as well as the diaphragm material/mass, can all be tailored to suit a desired use, such as intravenous cannulation.

The retraction of the puncture member may be automatic upon experiencing a pressure at or beyond a predetermined pressure difference from ambient. The retraction mechanism may actuate the puncture member in response to a predetermined positive or negative pressure differential. Advantageously, the device does not require pre-pressurisation for correct operation and can be ready for use at an ambient internal pressure.

In one embodiment, the device comprises a housing for the retraction mechanism and the puncture member depends from the housing such that the free end of the puncture member is spaced from the housing. The puncture member may be insertable into a sleeve such that the sleeve abuts against the housing. The puncture member and/or housing may be arranged to form a friction fit with the sleeve in use. The housing may comprise one or more formations for fitment with the sleeve member. A push-fit or twist-fit engagement formation may be provided on the housing.

The retraction mechanism may comprise a chamber and an engagement member which may be releasably engageable with the puncture member in response to change in the fluid pressure within the chamber. The hollow puncture member may have an opening spaced from the end of the puncture member. The opening may open into the chamber so as to allow fluid communication between the end of the puncture member and the chamber. Accordingly a fluid pressure at the end of the needle may be experienced in the chamber.

The retraction mechanism may comprise an actuator which is arranged to move the engagement member selectively out of engagement with the puncture member in response to the pressure within the chamber. The puncture member may be biased towards the second condition, for example by a spring. The biasing means may be coupled between the puncture member and the chamber and/or retraction mechanism housing. The engagement member may hold the puncture member against the biasing force of the biasing means and may allow retraction of the puncture member when disengaged there-from.

The puncture member may comprise an engagement formation for cooperation with the engagement member. The engagement member may comprise a protrusion depending radially outwardly from the puncture member.

The retraction mechanism may comprise a stop member to prevent further retraction of the puncture member beyond a predetermined distance. The stop member may be arranged to abut against the engagement formation of the puncture member in the second condition. The positioning of the stop member advantageously allows for reliable retraction of the puncture member by a predetermined distance.

The retraction mechanism may comprise a, inflatable member, such as a diaphragm member coupled to, or formed with, the chamber, which is moveable in response to the fluid pressure in the chamber. The engagement member may be actuable by the inflatable member and may be attached thereto or depend there-from. The inflatable member or diaphragm member may serve as a pressure sensor.

Additionally or alternatively the retraction mechanism may comprise an electronic pressure sensor for detecting fluid pressure within the chamber. In such an embodiment, the actuator may comprise an electrically or electronically operated actuator.

The puncture member may be elongate in form and may have a longitudinal axis. The retraction mechanism may actuate the puncture member between the first and second conditions in a substantially axial direction.

In one embodiment, the device comprises the sleeve. The sleeve may have an open end, through which the puncture member protrudes in the first condition. The open end of the sleeve may be immediately adjacent the end of the puncture member in the first condition. The sleeve is preferably a close or tight fit about the puncture member at its end. In the second condition, the sleeve and the housing preferably remain fastened together at a location spaced from the end of the puncture member. The puncture member is typically elongate in form and has a second end which is supported within the housing.

The puncture member and sleeve are typically formed of different materials. The puncture member may be formed of metal whereas the sleeve may be formed of a polymer material. In alternative embodiments, the puncture member and sleeve may be formed of the same material, such as, for example, a metal. Such an embodiment may comprise a two-part needle arrangement.

In one embodiment, the device comprises a medical device which may take the form of a cannula insertion device. The sleeve may comprise a cannula, which may be a ported cannula.

It will be appreciated by the skilled person that the term "vessel" used herein may constitute a conduit, a cavity or a reservoir and should be construed accordingly.

Practicable embodiments of the invention are described in further detail below with reference to the accompanying drawings, of which:

Figure 1:
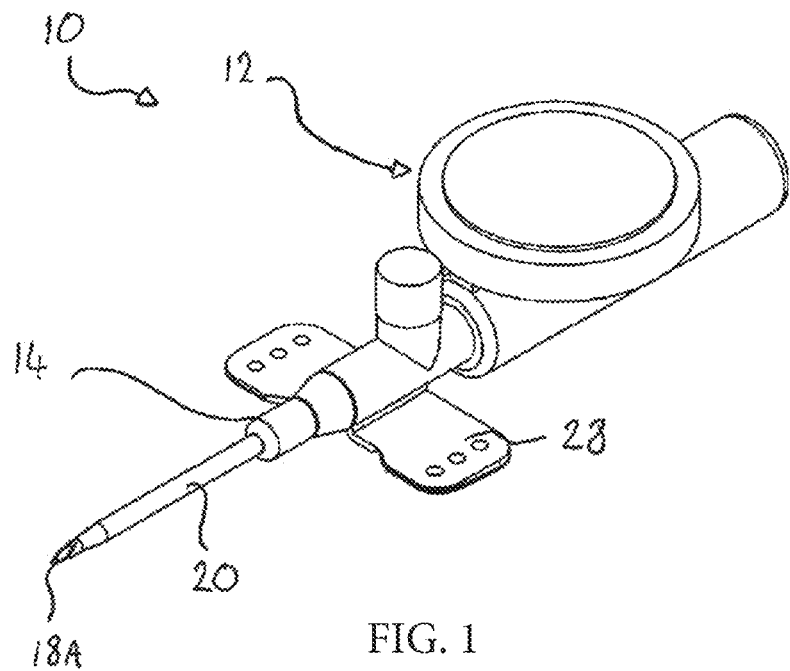
FIG. 1 shows a three-dimensional view of an assembly comprising a device and sleeve according to a first embodiment of the present invention.
Figure 2:
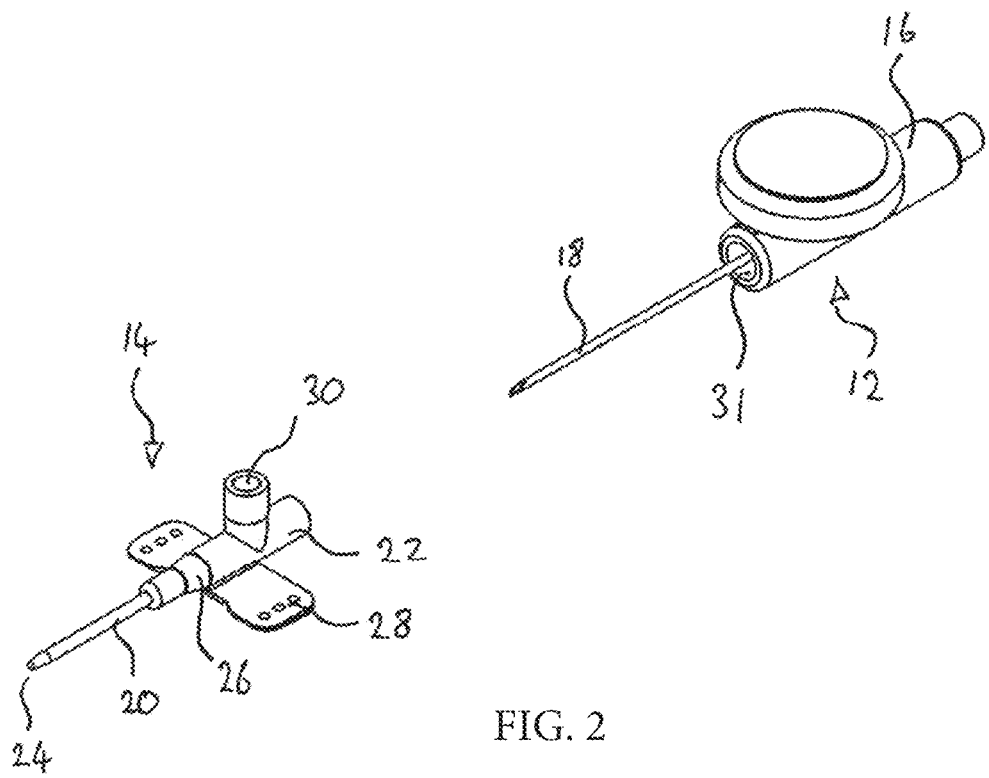
FIG. 2 shows the assembly of FIG. 1 with the device and sleeve disassembled.

The invention to be described below derives from the conception of an automatic mechanism to cause withdrawal of the puncture device out of a fluid vessel once a sleeve is correctly positioned for communication with the fluid vessel. In the case of a medical device for insertion of a sleeve such as a cannula into a fluid vessel within a body, the device is triggered when the needle moves from surrounding tissue into the vessel. This removes the need for the operator to manually retract the needle upon determination of the correct location of the needle in, for example a vein. The automation of this part of the process mitigates against a major cause of cannula insertion failure due to poor detection of the instant the vein is punctured.

This invention may trigger automatic withdrawal of the puncture member as soon as the sleeve is inserted into the vessel based on the change in pressure between the fluid in the vessel and the fluid or other matter outside of the vessel.

Whilst the invention finds particular use in the insertion of a conduit into a fluid vessel in the body, it is not limited to vascular access applications and may be used in other instances where it is necessary to undertake such an operation with minimal loss of fluid and/or where manual control of the operation is prone to potential failure.

Turning to FIGS. 1 to 5 there is shown a first embodiment of an assembly 10 and device 12 according to the invention, which may be used for percutaneous vascular access. The assembly 10 generally comprises a puncture device 12 and sleeve arrangement 14. The device comprises a housing 16 and a puncture member 18, in the form of a needle, depending there-from.

The sleeve arrangement 14 takes the form of a cannula which may be conventional in design, having an elongate plastic or metal tube 20 depending from a support formation 22. The tube 20 is of generally constant diameter but with a tapered formation towards its free end 24. The tube 20 has a longitudinal axial bore which opens into the interior of the support formation 22 such that the sleeve arrangement is substantially hollow along its entire length. The bore through the support formation is of greater diameter than that through the tube formation and has a tapered wall 26 by way of a neck portion which joins a tube-engaging end of the support formation to its main body.

The sleeve arrangement 14 also comprises lateral protrusions in the form of lobes 28 depending outwardly from the longitudinal axis which are located against the surface of a patient's skin during use.

The sleeve arrangement in this embodiment is 'ported' in that it has a further port 30 depending substantially radially outwardly from the body of the support formation. The port 30 provides a side duct which feeds into the cavity of the support formation to allow fluid communication with the tube 24. In alternative embodiments, this duct 30 may be omitted.

The device 12 comprises a recess 31 about the region of entry of the needle 18 into the housing 16. The recess 31 is shaped to form a friction fit about the open end of the support formation 22 of the sleeve 14. The recess 31 may be slightly tapered or otherwise shaped to provide a tight fitment with the sleeve 14. In alternative embodiments, the sleeve and/or housing 16 may comprise corresponding fixing formations so as to allow for a twist-fit engagement there-between.

The sleeve 14 is fixed to the housing for use in a manner shown in FIG. 1, such that the needle tip 18A protrudes slightly beyond the free end 24 of the cannula tube 20. In this regard, the needle end 18A is tapered to provide a sharp puncturing formation at the end of a main tube portion which is of substantially constant diameter along its length. The taper in the tubular needle construction forms an end opening, which is obliquely oriented relative to the longitudinal axis of the needle, and which is generally elliptical in plan. The sleeve end 24 is arranged in use as close a practicably possible to the edge of the opening in the needle at end 18A.

The arrangement of the sleeve 14 and the connection thereof to the device 10 is generally common to all embodiments to be described in relation to FIGS. 3-17 below and will not be repeated for conciseness. Whilst the invention is primarily concerned with the operation of the device itself, the device is configured for use with such a sleeve and is typically distributed as an assembly in which the device and sleeve 14 are assembled in a ready-to-use condition.

Figure 3:
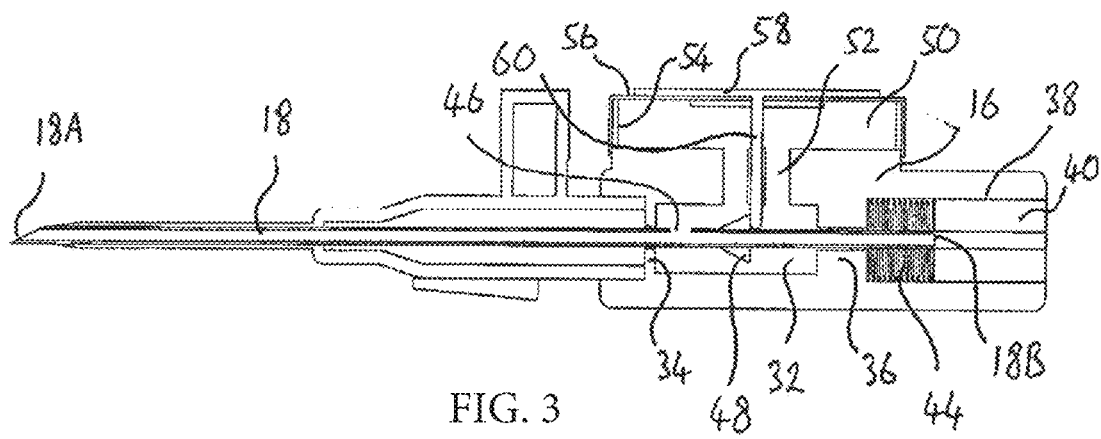
FIG. 3 shows a longitudinal section through the assembly of FIG. 1 in a first condition.
Figure 4:
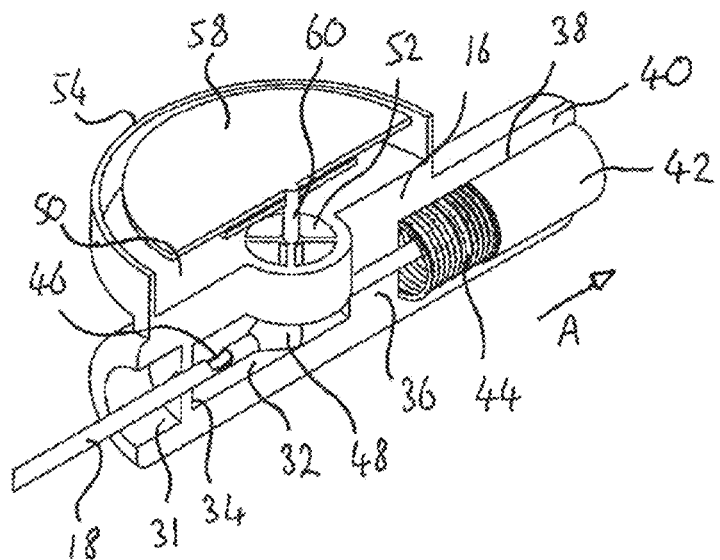
FIG. 4 shows a three dimensional view of the longitudinal section of FIG. 3.
Figure 5:
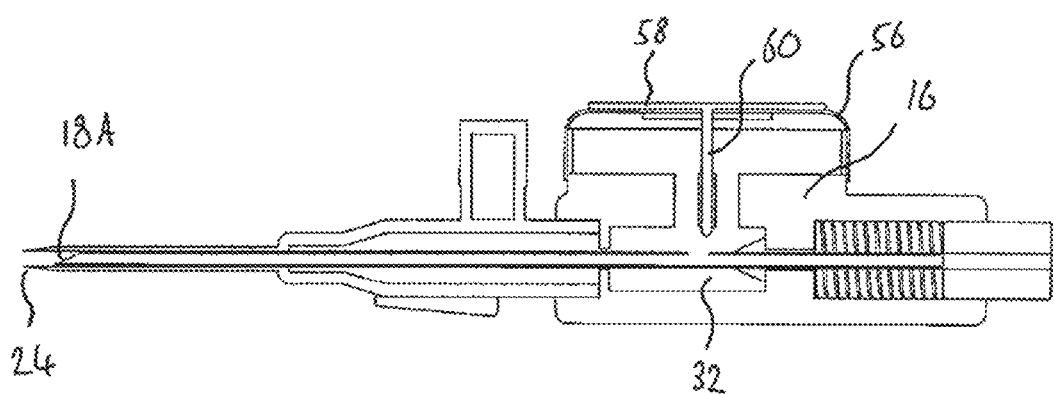
FIG. 5 shows a longitudinal section of the assembly of FIG. 1 in a second condition.

Turning now to FIGS. 3-5, the device 12 and its operation with respect to the sleeve will now be described.

The device housing 16 is shaped so as to define an internal chamber 32. The chamber 32 has front 34 and rear 36 end walls with openings therein aligned with the longitudinal axis of the needle 18 and shaped to closely surround the needle 18 in a fluid tight manner. In this embodiment, the chamber 32 is generally cylindrical in shape although it need not be limited to such a configuration.

On the opposing side of the rear wall 36 to the chamber 32 is a rear bore or recess 38, defined by a rearwardly extending cylindrical portion 40 of the housing 16. A body 42 in the form of a bung or stop is located in the recess 38 and is moveable in an axial direction there-in. The body 42 is biased in a rearward, retraction direction (as shown by arrow A) by biasing member 44, which in this embodiment takes the form of a coiled spring. The body 42 is braced against the internal wall 36 of the housing, with the spring 44 trapped in compression there-between.

The needle 18 is elongate in form and extends from end 18B which is mounted in the housing 16, specifically in the body 42 within the housing, through the chamber 32 and the walls 34 and 36 thereof to its free end 18A which is spaced from the housing. Accordingly the needle is mounted in the housing and depends there-from.

Within the portion of the needle 18 that passes through the housing chamber 32, there is provided an opening 46, part way along its length.

The portion of the needle 18 that is within the housing chamber 32 is also provided with an engagement formation 48 which depends radially outwardly from the needle body. The engagement formation may take the form of a tapered or ramped stop member, which may be frusto-conical in shape.

The chamber 32 communicates with a further chamber 50, which is typically larger in width, via a throat formation 52. The further chamber is defined by a base portion and a peripheral wall 54 which is upstanding from the remainder of the housing 16 and which is generally circular in plan. In alternative embodiments, the chamber need not be cylindrical but may take any suitable shape in order to allow a sufficient size of diaphragm to be accommodated. The base and upstanding wall 54 are integrally formed with the remainder of the housing 16.

The chamber 50 is sealed from the outside of the device by a diaphragm 56 (omitted from FIG. 4), which is attached about the peripheral face of the wall 54. The diaphragm comprises a deformable material, such as a polymer, so as to allow movement thereof in response to pressure changes between the interior of the chamber 54 and the exterior of the device. The diaphragm is typically shaped according to the shape of the chamber 50.

The diaphragm is typically offset from the longitudinal axis of the device and/or needle. The diaphragm may be actuable in a direction which is substantially perpendicular to such an axis. The diaphragm and chamber may be greater in width than the remainder of the device.

The diaphragm 56 is sandwiched between opposing discs 58 which provide further rigidity to the diaphragm assembly. Protruding from the outer disc 58 towards the needle 18, there is provided an engagement formation in the form of a pin 60. In this embodiment, the pin 60 is integrally formed with the outer disc 58 and extends through the diaphragm 56 and inner disc towards the chamber 32. A guide formation is provided within the throat 52, through which the pin 60 extends.

Whilst chambers 32 and 50 are formed within the housing as separate chambers, connected by throat 52, it will be appreciated that those chambers are maintained at a substantially uniform pressure and accordingly those chambers may be combined in an alternative embodiment.

In the first condition shown in FIG. 3, the pin 60 engages with the engagement formation 48 of the needle 18 and prevents retraction of the needle by the spring 44. Thus the device is in a primed condition, ready for insertion into a fluid vessel. In this condition, the needle tip 18A protrudes beyond the free end of tube 20 in the manner described above. The pressure within chambers 32 and 50 are equal to the exterior pressure since the chambers communicate with the outside of the device via the needle bore and opening 46 therein. Accordingly the diaphragm is in an at rest condition since the pressure inside and outside the device is equalised.

In use, the tip of the needle 18A and associated cannula 20 is inserted into the body of a patient. As the needle tip 18A passes through tissue, the pressure inside the device does not substantially change since little or no fluid enters the needle 18. However once the needle enters a fluid vessel in the body, by piercing the vessel wall, the interior chambers 32 and 50 are exposed to the fluid pressure within the vessel.

The passage of fluid through fluid vessels requires a fluid pressure differential to exist. Accordingly, upon the entry of the needle tip 18A into the fluid vessel, a pressure gradient is established between the chambers 32, 50 and the vessel interior. In the example of a blood vessel, such as a vein, or other 'flowing' vessel, the pressure in the vessel is typically greater than ambient pressure (i.e. the pressure within the device 12). Accordingly fluid will tend to flow into the chambers 32, 50 and thereby actuate the diaphragm by inflation.

The actuation of the diaphragm away from the needle 18 (i.e. by inflation) causes the pin 60 to move radially away from the needle axis and thereby disengage the engagement formation 48. Once disengaged, the needle moves axially rearward under the biasing force of the spring 44 on the body 42 until the engagement formation 48 abuts against chamber wall 36. Thus the needle is retracted relative to sleeve 14 by a predetermined distance (i.e. the distance between the engagement formation 48 and the wall 36 in FIG. 3), so as to achieve the condition shown in FIG. 5.

The increase in pressure in the chambers 32, 50 may be achieved by the flow of fluid from the vessel into the chambers and/or compression of any existing fluid (e.g. air) which may already be present in the chambers. Also the required distance of travel of the pin is relatively small. Accordingly the device is particularly sensitive and requires only a minimal fluid flow for actuation.

FIG. 5 represents the deployed condition in which the needle end 18A is contained within the tube 20 and the body 42 protrudes rearwardly beyond the end of the housing 16. The diaphragm is maintained in its actuated condition. The body 42 in this condition also advantageously provides a visual indication to a user that the needle has been retracted. In this regard the body 42 may be coloured or otherwise marked such that it is clearly visible once it protrudes beyond the housing 16. However in alternative embodiments, the body 42 may not protrude beyond the end of the housing 16 such that the actuation of the device cannot be inadvertently hindered by an operator.

The retraction of the needle 18 as described above leaves the tube 18, in this embodiment, the cannula, correctly located in the fluid vessel. The actuation pressure and spring force involved are sufficiently small that there is minimal disturbance to an operator holding the device 12. It is also advantageous that the needle is at the same time made temporarily safe, such that it is no longer exposed and cannot accidentally puncture the fluid vessel further.

The device 12 is removed from the sleeve 14 completely. The sleeve arrangement 14 can be secured in place against a patient's skin in a conventional manner, such that the cannula remains in place against the patient's skin for further use, such as the administration of fluid to, or else removal of fluid from, the vessel. The sleeve is typically secured after removal of the device 12 but may be secured whilst the device remains assembled therewith if necessary.

The embodiment above utilises a disc-shaped diaphragm to effect movement of the release pin when the fluid pressure reaches a certain threshold. The rigid disc components above and below the diaphragm ensure that there is uniform inflation of the diaphragm, and hence a predictable effect on the release pin.

Sensitivity of the device to fluid pressure differentials is important to correct operation, and the desired sensitivity is achieved by tailoring the enlarged area of the diaphragm such that it can actuate the mechanism under relatively low pressures, whilst avoiding unwanted actuation of the device when not in use.

In an alternative embodiment, it is possible that a stack of diaphragms could be used to increase sensitivity in addition to, or instead of, the enlarged area diaphragm shown in FIGS. 1-5. This may help reduce the overall size of the device.

In order to further increase the accuracy with which the device can operate, the underside of the needle tip 18A (in the orientation shown in FIG. 3) may be provided with a small opening such that fluid can escape the needle up until the point at which the whole of the needle opening is located in the vessel. This secondary opening in the wall of the main end opening of the puncture member can prevent early actuation of the device as the puncture member enters the vessel. It is important that the end of the cannula has entered the vessel when the fluid pressure increases within the needle, and hence the needle retracts, in order that the cannula is successfully inserted into the vein. The secondary opening in the wall of the needle may be provided immediately adjacent to the cannula end.

Figure 6:
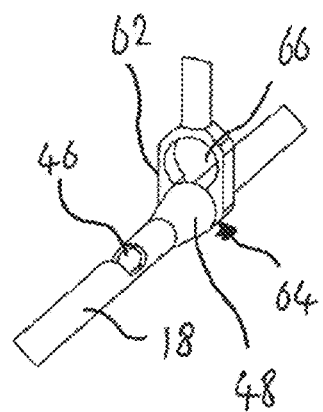
FIG. 6 shows a three-dimensional view of an alternative arrangement between the actuator and puncture member according to a second embodiment of the invention.
Figure 7:
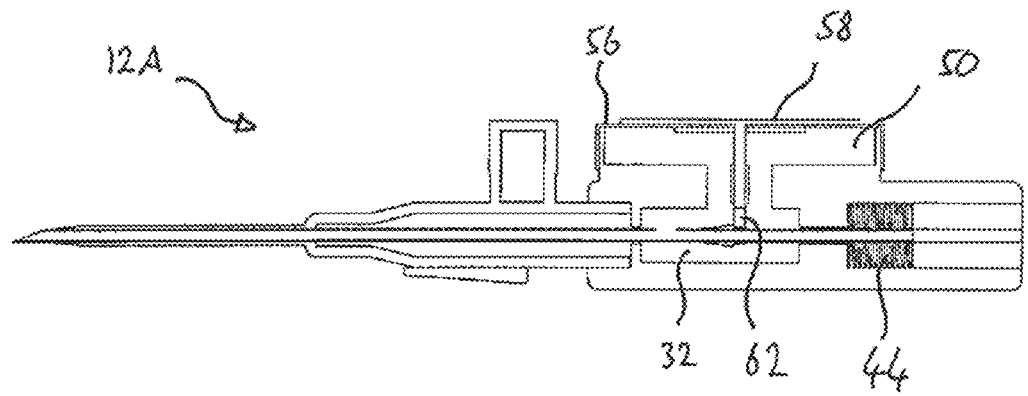
FIG. 7 shows a longitudinal section through the assembly according to the second embodiment in a first condition.
Figure 8:
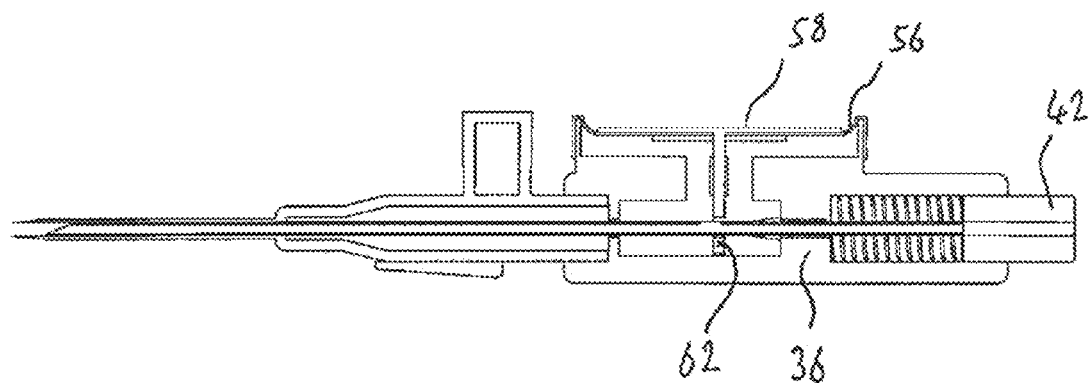
FIG. 8 shows a longitudinal section through the assembly according to the second embodiment in a second condition.

In FIGS. 6-8, there is shown a further embodiment of the invention, which allows for actuation of the device 12 when the puncture member 18 is inserted into a fluid vessel of lower pressure than that in the chambers 32, 50 within the device. The construction of device 12A of FIGS. 6-8 is the same as the device of FIGS. 1-5 described above save that the engagement pin 60 is provided with a head formation 62 as shown in FIGS. 6-8.

The head formation 62 has a pair of adjoining apertures 64, 66 therein. The first aperture 46 has a diameter which is slightly larger than the diameter of the needle 18 but less than that of the engagement formation 48. The second aperture 66 adjoins the first aperture 64 and has a diameter which is greater than that of the first aperture and the engagement formation 48. The first aperture 64 is located furthest from the disc 58 (i.e. towards the outer end of the head formation 62), whilst the second aperture 66 is located between the first aperture and the disc (i.e. proximate the pin shaft 60).

In the first, primed, condition shown in FIGS. 6 and 7, the head formation 62 engages the engagement formation 48 of the pin 18 against the biasing force of the spring 44 in a manner similar to that of FIG. 3. However, in use, when the needle tip 18A of the device 12A is inserted into a fluid vessel of lower pressure than that inside the device 12A, the diaphragm will experience a negative pressure differential, thereby causing actuation of the diaphragm 56 and disc 58 towards the needle axis as shown in FIG. 8.

The actuation of the diaphragm, disc 58 and the associated head formation 62 as shown in FIG. 8 causes the larger aperture 66 to become aligned with the engagement formation 48, thereby disengaging formation 48 and allowing retraction of the needle into the second condition shown in FIG. 8 until the engagement formation 48 abuts the chamber wall 36.

Accordingly the changing of the engagement member 60 can allow for the device to operate under positive or negative pressure differentials. This allows application of the present invention to a wider variety of anatomical vessels, including cavities having a fluid pressure which is typically below atmospheric pressure.

Turning now to FIG. 9, there is shown two further embodiments of an assembly according to the present invention, which comprise the device 12 or 12A of either the first or second embodiment described above. The embodiment of FIGS. 9-11 is provided with a cover, which is formed of a rigid material, such as the plastic used to form the housing 16. The cover is shaped to be attached about the peripheral wall 54 of the device such that it covers the diaphragm 56 and disc 58.

The cover acts as a lid or cap and is shaped to form an internal space between the diaphragm 56, including disc 58 and the cover so as to allow movement of the diaphragm in use. The cover prevents access to the diaphragm which may cause unwanted or accidental actuation of the diaphragm 56 prior to the intended use of the device.

Figures 9A, 9B:
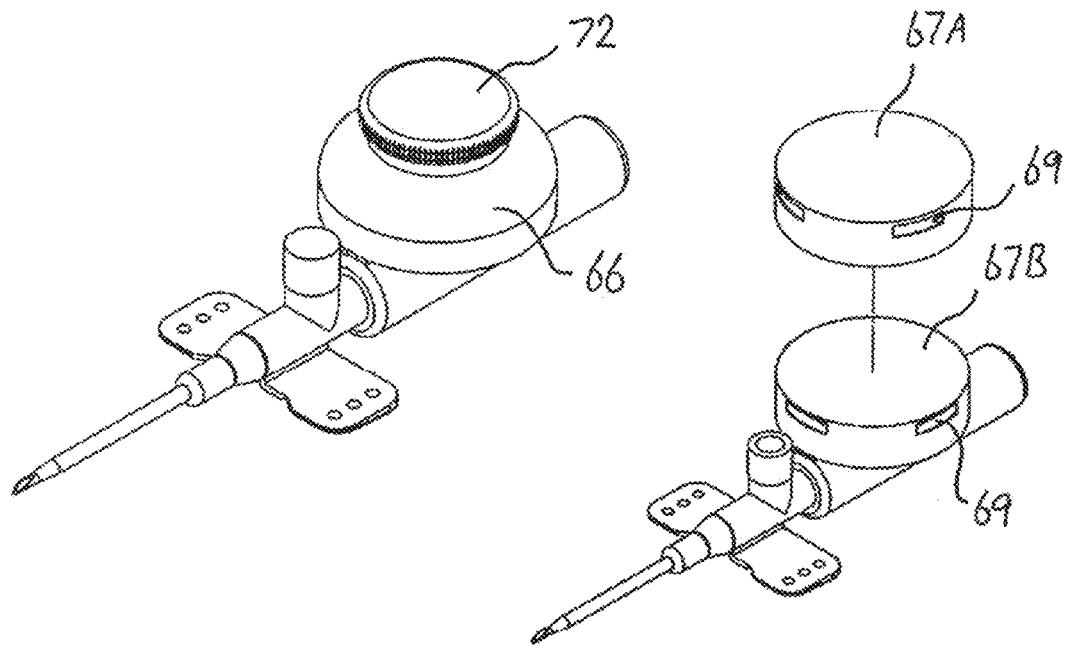
FIG. 9A shows a three-dimensional view of an assembly comprising a device, a sleeve and a cover according to a third embodiment of the present invention.
FIG. 9B shows another three-dimensional view of an assembly comprising a device, a sleeve and a cover according to the third embodiment of the present invention.
Figures 10, 11:
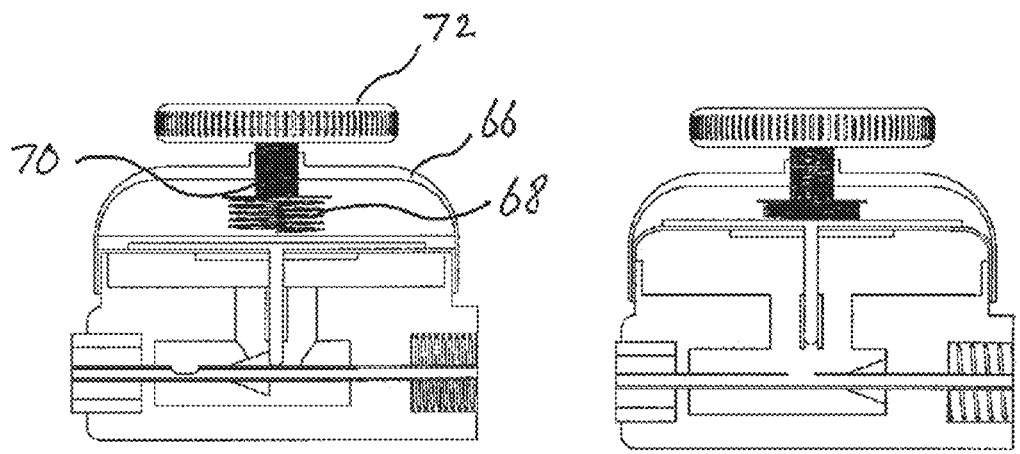
FIG. 10 shows a longitudinal section through the device according to the third embodiment in a first condition.
FIG. 11 shows a longitudinal section through the device according to the third embodiment in a second condition.

Although not shown in FIG. 9A, the cover will typically have an air inlet to ensure that the outer face of the diaphragm is exposed to ambient pressure. The size of this air inlet will affect the response of the diaphragm to changes in the needle fluid pressure, and hence the air inlet may be variable in size to enable adjustment of sensitivity, although it is generally preferred to avoid choking of any flow to, or from, the diaphragm through the cover to achieve a short time delay in the actuation of the device.

One embodiment of such an adjustable cover is shown in FIG. 9B, for which the cover comprises first and second cover members 67A and 67B. The cover member 67B is seated over the diaphragm and associated chamber of the device. The cover member 67A is of slightly larger size than cover member 67B such that it can be located over the cover member 67B. Both cover members have an aperture therein 69 such that the degree of overlap between the apertures of the cover members 67A and 67B determines the size of the window or air inlet. The cover 67A can thus be rotated to adjust the aperture size. The apertures 69 in the cover members are preferably elongate in form and circumferentially aligned to facilitate easy and accurate adjustment thereof.

The cover 66 in the embodiment of FIGS. 9A, 10 and 11 also includes means for adjusting the resistance of the diaphragm to motion by way of biasing member 68, in the form of a spring. The spring may resist motion under the compression, or extension, of the spring such that, in order to actuate the device, the pressure differential must be sufficient to overcome the resilience of the spring. The spring may also serve to dampen the motion of the diaphragm and ensure a smooth operation of the device.

The spring 68 is mounted on an adjustable shank 70 which is received in a corresponding port in the cover 66. Thus the resilience offered by the spring 68 can be adjusted so as to allow adjustment of the threshold pressure at which the device is actuated between the first and second conditions. In this example, the shank 70 and cover aperture are correspondingly threaded. The shank is provided with a thumb screw or knob formation 72 or similar manual adjustment formation such that the degree of compression or extension of the spring 68 can be easily adjusted by hand. One or more indicia may be provided on the cover to show pre-set threshold condition such that an operator can adjust the formation 72 by a set number of turns or fractions of a turn to achieve the desired threshold setting. The features of FIGS. 9A-11 and FIG. 9B may be combined.

Figure 12:
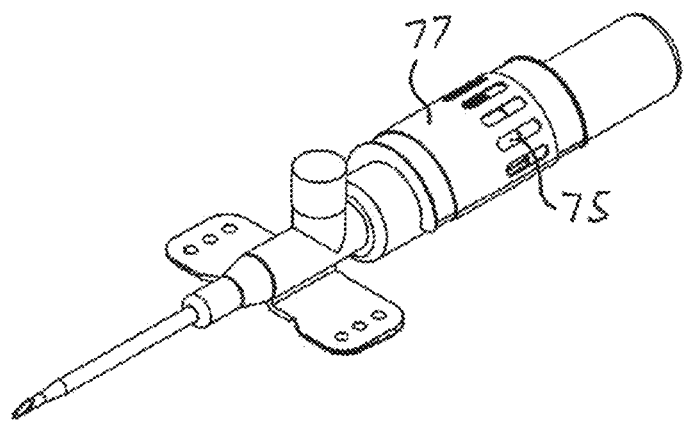
FIG. 12 shows a three-dimensional view of an assembly comprising a device and sleeve according to a fourth embodiment of the present invention.
Figure 13:
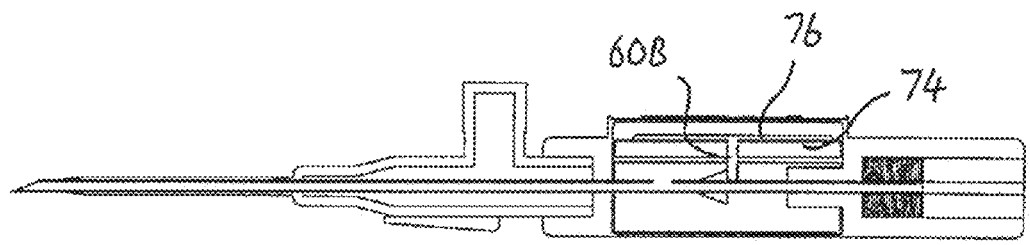
FIG. 13 shows a longitudinal section through the assembly of FIG. 12 in a first condition.
Figure 14:
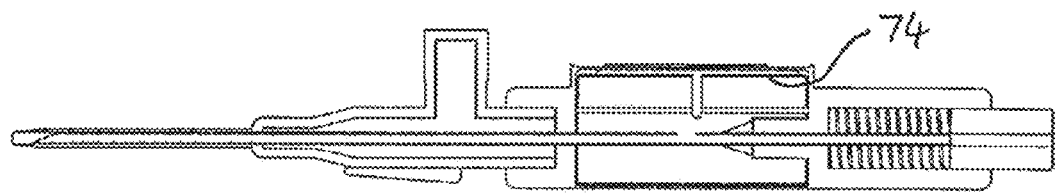
FIG. 14 shows a longitudinal section through the assembly of FIG. 12 in a second condition.

In FIGS. 12-14, there is shown a further embodiment 12B of the invention which is the same as that of any of FIGS. 1-8 described above, save that the modified device housing 16B no longer has the chamber 50, nor the diaphragm 56 or associated discs 58. Instead, the chamber 32B has been modified to house a different type of diaphragm, in the form of balloon 74, which may be considered to provide a longitudinal or concave type diaphragm. In the first, un-actuated, condition the balloon only partially fills the chamber 32B. The balloon 74 may be formed of a material similar to that used for inflation of stent balloon devices as is known in the field of medical apparatus. The balloon is provided with one or more rigid ribs or rods 76, which support the engagement formation 60B, and which are arranged substantially parallel with the longitudinal axis of the needle 18. The ribs may accordingly be considered to be longitudinal in design.

Also the device housing 16B has a number of apertures 75 therein. The device also comprises a cover in the form of collar, or partial-collar, member 77 with corresponding apertures therein. The position of collar 77 on housing 16B is adjustable so as to vary the size of the opening to allow fluid communication with the exterior of the balloon 74 such that the balloon can freely inflate and deflate in a manner similar to that described in relation to FIG. 9 above. The collar 77 is moveable in an axial direction in this embodiment but alternative actuation of the cover is feasible dependent on the shape and orientation of the apertures.

The embodiment of FIGS. 12-14 operates in a manner similar to that of FIG. 3-5 or 6-8 described above such that the pressure differential caused by insertion of the needle into a fluid vessel causes inflation or collapse of the balloon 74 so as to release the engagement formation 48 and thereby allow retraction of the needle 18 into the sleeve.

Other embodiments of inflatable, or pressure sensitive, actuation devices will be apparent to the skilled person as alternatives to the embodiments described above and may be substituted for the actuation mechanisms described above provided the required pressure sensitivity characteristics can be achieved. Such embodiments may, for example comprise a bellows configuration or a low-friction piston arrangement.

Figure 15:
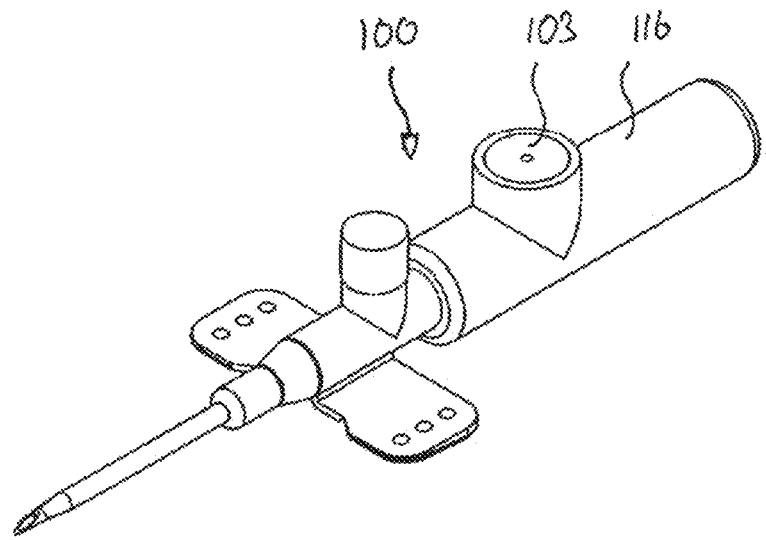
FIG. 15 shows a three-dimensional view of an assembly comprising a device and sleeve according to a fifth embodiment of the present invention.
Figure 16:
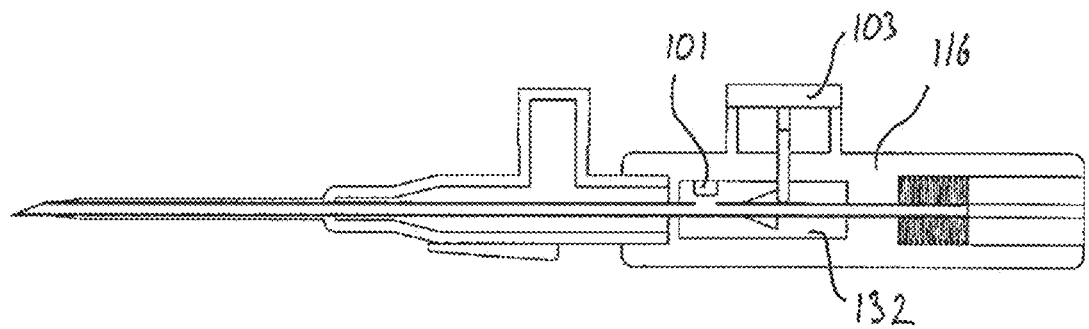
FIG. 16 shows a longitudinal section through the assembly of FIG. 15 in a first condition.
Figure 17:
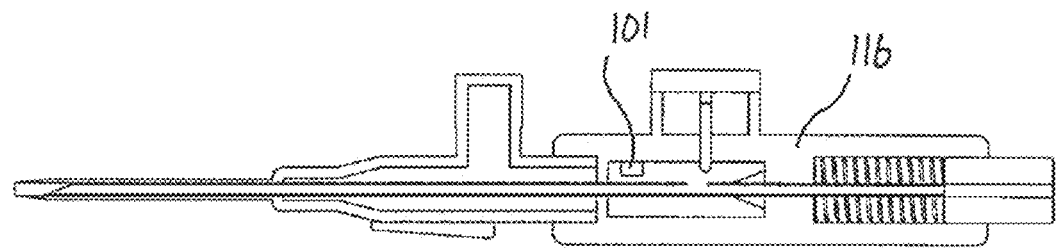
FIG. 17 shows a longitudinal section through the assembly of FIG. 15 in a second condition.

Turning now to FIGS. 15-17 an alternative embodiment 100 is shown, which allows for electronic control of the actuation of the device instead of the purely mechanical sensing and actuation means proposed in the above-described embodiments.

The embodiment 100 of FIGS. 15-17 is similar in construction and operation to the embodiments described above, save for the following differences.

The housing 116 has been modified to provide a single internal chamber 132, in which is mounted an electronic pressure sensor 101. A processor is provided (not shown) to compare the pressure sensed by sensor 101 to a preset threshold pressure and to control operation of an actuator when the sensed pressure meets or exceeds the threshold value. The processor may take the form of a simple comparator or else a more complicated programmable chip dependent on the level of sophistication required for the intended operation. The actuator in such an embodiment may comprise an electric or electronic actuator such as, for example, a solenoid 103, which is arranged to displace engagement member 160 in a manner similar to that described above. A power source such a batter will typically also be provided to power the actuation mechanism.

Whilst the embodiments described above make use of a continually biased needle arrangement, since it allows for actuation of the needle under a relatively small pressure differential, as will typically be experience in medical applications, it is also possible the actuator may displace the needle directly, rather than disengaging a latching means for the needle. For example, in an electronically controlled embodiment in particular, a solenoid or other powered actuator will typically be sufficient to drive the retraction of the needle itself in a reliable manner without the need to bias the needle to a retracted condition in advance.

The threshold pressure may be different for different patients. However, it is likely that the device will have a standard threshold, although possibly with a setting for low pressure patients (such, as for example, for elderly patients or those suffering blood loss). The fluid pressure may also be higher than normal vein pressure, due to the presence of a tourniquet, and the threshold pressure may be adjusted or preset accordingly. A value of between 15-25 mm Hg and, typically around the value of 20 mm Hg, hydrostatic pressure is proposed as being a normal threshold.

Figures 18A, 18B:
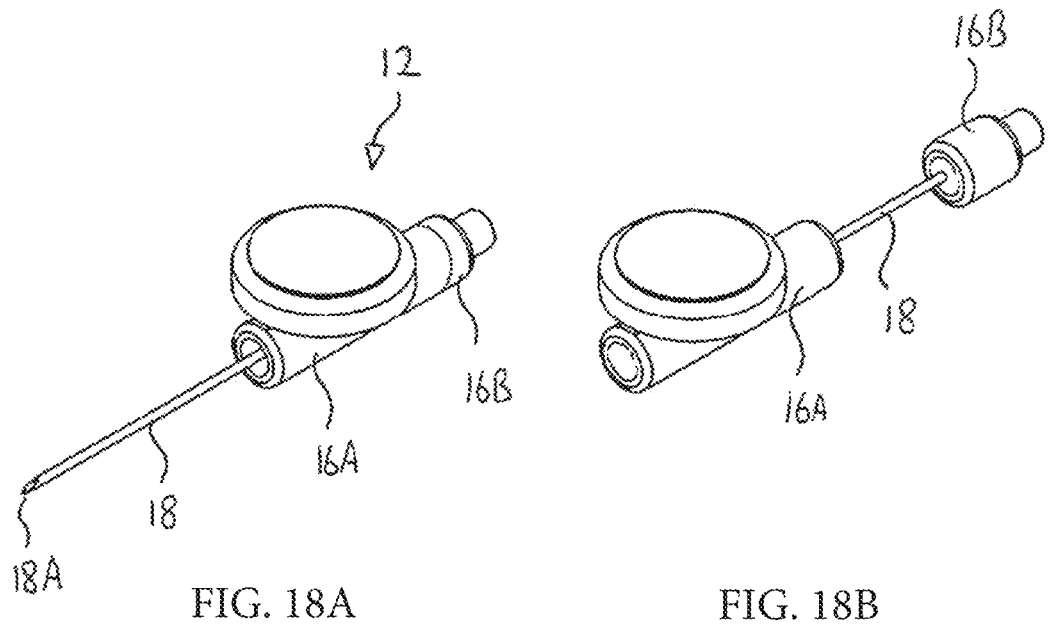
FIGS. 18A and 18B show further optional features of a puncture device according to the invention; and, FIG. 19 shows an additional or alternative safety feature to the arrangement of FIGS. 18A and 18B.

Turning now to FIGS. 18A and 18B, there is shown the device 12 of FIGS. 1-5 comprising a safety feature to allow the needle 18 to be made safe after use. In this example, the device housing 16 is formed of two parts 16A and 16B. The needle 18 is mounted in part 16B. The two housing parts 16A and 16B are firmly held together during use of the device but are detachable. This may be achieved by an attachment arrangement similar to that described above between the device 12 and sleeve arrangement 14 and may comprise a frictional engagement, such as a push-fit engagement, between correspondingly shaped and/or closely fitting formations. Other conventional engagement arrangements, such as a twist-fitting or locking engagement, may be used.

After the device has been used as described above, the housing part 16B, in which the needle is mounted, can be pulled apart from housing part 16A until the end 18A of the needle is located within the housing part 16A. Thus the device is made safe for disposal. A simple mechanism, such as a spring loaded plate, can be used to limit the available distance of separation of the housing parts 16A and 16B and/or to lock the needle in its made-safe condition within housing portion 16A.

Figure 19:
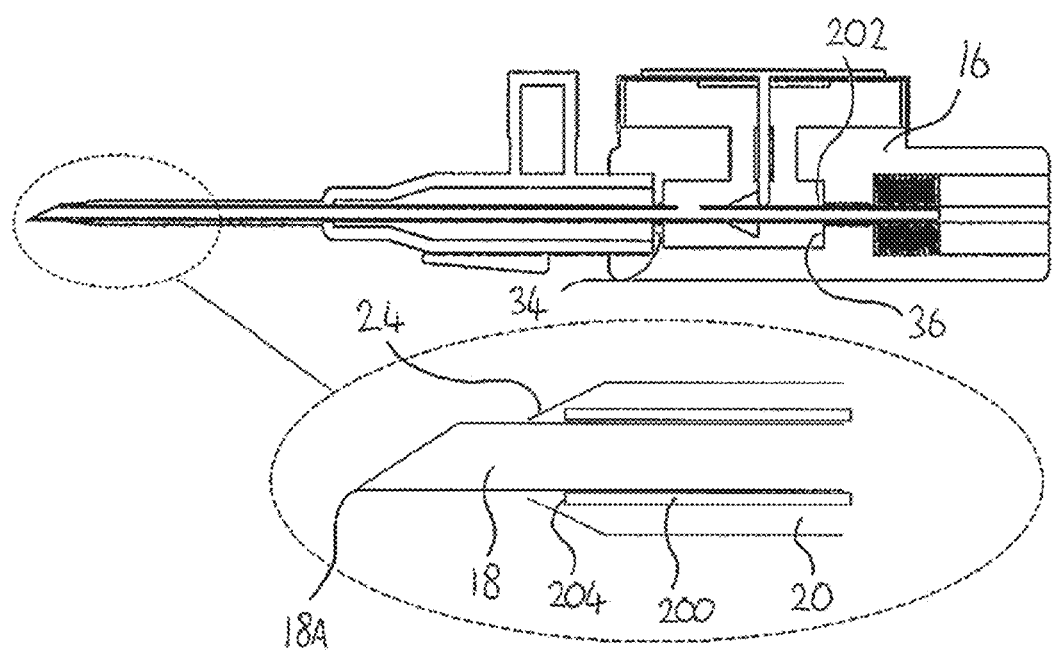

Turning now to FIG. 19, optional features of the device of any preceding embodiment are shown in an enlarged window. The needle 18 may comprise a sheath or tube 200 which is concentric therewith and extends in the same axis as the needle. The tube 200 is blunt at its free end and may be formed of a suitable plastic or other material. The tube is mounted at its fixed end 202 within the device 12. However, unlike the needle 18, the tube 200 is fixedly attached to a rigid portion of the device housing 16, such as an internal wall thereof (e.g. wall 34 or 36) and is not actuable thereto.

The tube is maintained within the sleeve 20.

In use, the needle end 18A protrudes beyond the free end 204 of the tube. In this condition, the free end 204 of the tube is also behind the free end 24 of the sleeve 20 such that it does not interfere with the operation of the device as described above. However, upon retraction of the needle, the needle is actuated relative to the fixed tube such that it is withdrawn beyond the free end 204 of the tube. Thus when the device 12 is removed from the sleeve arrangement after use, the needle end 18A remains within the tube 200, thereby avoiding accidental injury which may be caused by the exposed needle.

In the manner described above in relation to FIGS. 18 and/or 19, any of the embodiments of the invention described above can be provided with an anti-stab, or made-safe, feature.

The different medical uses for which the present invention may be applicable comprise, for example, intravenous cannulation, aspiration/drainage of fluids within body cavities (e.g. pleural effusions, ascites), and/or laporoscopy trochar. The cannula may also be substituted for an alternative sleeve, such as a metal sleeve for use as a two-part needle arrangement. It is also envisaged that the invention may be applicable to wider engineering use where a conduit is required to be placed in communication with an existing fluid vessel by first puncturing the vessel.

In any of the foregoing embodiments, the chamber within the housing may comprise a transparent material portion in the form of a window or the like so as to provide in use an indication to the operator that a fluid has entered the chamber. The use of such a visual indication of fluid entering the chamber provides a beneficial second means for checking correct operation of the device. Accordingly an operator can visually check correct deployment of the device using both the projection, to determine that the device has actuated, and also the window, to determine that fluid communication between the vessel and the chamber has been achieved.

The visual confirmation of one indication in the absence of the other may infer incorrect or incomplete operation of the device such that an operator can attempt to reposition the device, or undertake other steps to ensure correct operation, prior to removing the puncture member. In the event that fluid is seen via the window but the retraction mechanism has not actuated, the operator may manually retract the puncture member by withdrawing it from the sleeve so as to complete the operation.

In further embodiments, the device may comprise an additional or alternative alerting means such as an electronic system to sense retraction of the needle and alert the operator by way of a visual or audible indicator.

The invention claimed is:

1. A fluid vessel insertion device comprising:
   a sleeve attached to the fluid vessel insertion device in a fixed position; and
   a linearly movable puncture member configured to be located within the sleeve;
   a retractor configured for actuating the puncture member relative to the sleeve-between:
      a first condition in which an end of the puncture member protrudes beyond an end of the sleeve such that the puncture member may be inserted into the body of a patient, and
      a second condition in which the end of the puncture member is within the sleeve, wherein the end of the puncture member is a puncturing end with a first aperture for insertion into a fluid vessel in use;
   wherein the retractor comprises an internal chamber, the puncture member extending into the internal chamber and comprising a second aperture, which second aperture is in fluid communication with the first aperture, for fluid communication between the first aperture and the interior of the internal chamber, and a pressure sensor in the form of an inflatable member coupled to, or formed with, the internal chamber, the inflatable member being movable relative to walls that define the internal chamber in response to fluid pressure in the internal chamber;
   wherein said internal chamber is sealed from the exterior of the device except via the first aperture, and the internal chamber is maintained at an ambient pressure when the device is in an at-rest state,
   wherein retraction of the puncture member by the retractor from the first condition to the second condition is caused in response to the inflatable member sensing a positive external fluid pressure at the end of the puncture member that is greater than a predetermined pressure difference from ambient pressure,
   wherein the inflatable member is connected to a peripheral wall defining another chamber in fluid communication with the internal chamber,
   wherein the another chamber has a generally cylindrical shape, and
   wherein the inflatable member is movable relative to the peripheral wall.

2. The device according to claim 1, wherein the puncture member is hollow to allow said fluid communication between the first and second apertures.

3. The device according to claim 1, wherein the puncture member comprises a needle.

4. The device according to claim 1, comprising a housing comprising the retractor and the pressure sensor, wherein the internal chamber is entirely contained within the housing, and wherein the puncture member depends from the housing to its puncturing end.

5. The device according to claim 1, wherein the internal chamber is maintained at substantially ambient pressure in the at-rest state and the device is configured to trigger the retractor to actuate the puncture member into the second condition when a pressure gradient is experienced between an interior of the internal chamber and an external pressure at the end of the puncture member.

6. The device according to claim 1, wherein the inflatable member comprises a diaphragm.

7. The device according to claim 6, wherein the internal chamber comprises a rigid wall structure and the diaphragm comprises a flexible wall.

8. The device according to claim 6, wherein the internal chamber comprises a first portion of reduced width and a second portion of enlarged width, the diaphragm spanning the second portion of the internal chamber.

9. The device according to claim 1, wherein the retractor comprises an engagement member arranged to releasably engage the puncture member dependent on the pressure within the internal chamber.

10. The device according to claim 9, wherein the puncture member is biased towards the second condition and is releasably held in the first condition by the engagement member.

11. The device according to claim 1, comprising a stop member arranged to limit travel of the puncture member by the retractor to a predetermined distance.

12. The device according to claim 11, wherein the stop member is located in the internal chamber of the retractor and braced against a rear wall of the internal chamber when the retractor is in the second condition.

13. The device according to claim 12, wherein the stop member has a frustoconical shape.

14. The device according to claim 12, wherein the stop member is biased in a retraction direction by a biasing member disposed in the recess.

15. The device according to claim 1, comprising a housing for the retractor, wherein the puncture member depends from the housing such that a first end of the puncture member is spaced from the housing and a second end of the puncture member is mounted in the housing.

16. The device according to claim 1, wherein the inflatable member is a diaphragm sandwiched between two opposing discs.

17. The device according to claim 16, wherein a pin is integrally formed with an outer disc of the two opposing discs and extends through the diaphragm and an inner disc of the two opposing discs towards the internal chamber, and
   wherein a guide formation is provided within a throat through which the pin extends into the internal chamber.

18. The device according to claim 1, wherein the retractor further comprises an engagement member releasably engageable with the puncture member, the engagement member actuable by the inflatable member in response to sensing a positive external fluid pressure, which is greater than a predetermined pressure difference from ambient pressure, at the end of the puncture member.

19. The device according to claim 18, wherein the puncture member comprises an engagement formation for cooperation with the engagement member.

* * * * *